(12) United States Patent
Field et al.

(10) Patent No.: US 8,858,491 B2
(45) Date of Patent: Oct. 14, 2014

(54) PRE-BIASED MEMBRANE VALVE

(75) Inventors: Leslie A. Field, Portola Valley, CA (US); Robert Joseph Sanchez, Jr., Oceanside, CA (US); Matthew J. A. Rickard, Yorba Linda, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/478,169

(22) Filed: May 23, 2012

(65) Prior Publication Data

US 2013/0317413 A1  Nov. 28, 2013

(51) Int. Cl.
*A61M 5/00* (2006.01)

(52) U.S. Cl.
USPC ............................................................ 604/9

(58) Field of Classification Search
USPC ............................................................ 604/9
See application file for complete search history.

(56) References Cited

U.S. PATENT DOCUMENTS

| | | | | |
|---|---|---|---|---|
| 3,441,245 | A * | 4/1969 | Holland et al. | 251/5 |
| 3,759,289 | A * | 9/1973 | DeWall | 137/844 |
| 5,071,408 | A * | 12/1991 | Ahmed | 606/108 |
| 5,171,213 | A * | 12/1992 | Price, Jr. | 604/9 |
| 5,192,265 | A * | 3/1993 | Drake et al. | 604/10 |
| 5,397,300 | A * | 3/1995 | Baerveldt et al. | 604/8 |
| 5,968,058 | A * | 10/1999 | Richter et al. | 606/166 |
| 6,007,511 | A * | 12/1999 | Prywes | 604/9 |
| 6,050,970 | A * | 4/2000 | Baerveldt | 604/28 |
| 6,090,062 | A * | 7/2000 | Sood et al. | 604/9 |
| 6,186,974 | B1 * | 2/2001 | Allan et al. | 604/30 |
| 6,261,256 | B1 * | 7/2001 | Ahmed | 604/9 |
| 6,383,160 | B1 * | 5/2002 | Madsen | 604/10 |
| 6,468,283 | B1 * | 10/2002 | Richter et al. | 606/108 |
| 6,544,208 | B2 * | 4/2003 | Ethier et al. | 604/8 |
| 6,554,208 | B1 * | 4/2003 | Venuto, Sr. | 239/207 |
| 6,626,858 | B2 * | 9/2003 | Lynch et al. | 604/8 |
| 6,736,791 | B1 * | 5/2004 | Tu et al. | 604/8 |
| 6,855,770 | B2 * | 2/2005 | Pinchuk et al. | 525/240 |
| 7,226,540 | B2 * | 6/2007 | Rodgers et al. | 210/321.84 |
| 7,364,564 | B2 * | 4/2008 | Sniegowski et al. | 604/9 |
| 7,384,550 | B2 * | 6/2008 | Rodgers et al. | 210/321.84 |
| 7,431,709 | B2 * | 10/2008 | Pinchuk et al. | 604/8 |

(Continued)

FOREIGN PATENT DOCUMENTS

| | | |
|---|---|---|
| WO | WO 00/29770 | 5/2000 |
| WO | WO 00/37128 | 6/2000 |

OTHER PUBLICATIONS

International Search Report issued for PCT/US2013/042351 dated May 9, 2013, 4 pages.

*Primary Examiner* — Susan Su
*Assistant Examiner* — Guy K Townsend
(74) *Attorney, Agent, or Firm* — Haynes and Boone, LLP

(57) ABSTRACT

A method of manufacturing a valve for a fluid system is described herein. The method comprises determining a target cracking pressure for the valve of the fluid system, providing an inner wall having a first height and an outer wall having a second height, the first height varying from the second height by a height differential, and attaching a flexible membrane to the outer wall at the second height, wherein a central zone of the flexible membrane is in contact with the inner wall at the first height and the inner wall biases the flexible membrane from a neutral condition. The height differential is selected to provide resistance to displacement from the inner wall until pressure acting on the membrane exceeds the target cracking pressure.

18 Claims, 3 Drawing Sheets

(56) References Cited

U.S. PATENT DOCUMENTS

| | | | |
|---|---|---|---|
| 7,488,303 B1 * | 2/2009 | Haffner et al. | 604/8 |
| 7,544,176 B2 * | 6/2009 | Rodgers et al. | 604/9 |
| 7,670,310 B2 * | 3/2010 | Yaron et al. | 604/9 |
| 7,850,637 B2 * | 12/2010 | Lynch et al. | 604/8 |
| 7,857,782 B2 * | 12/2010 | Tu et al. | 604/8 |
| 7,862,531 B2 * | 1/2011 | Yaron et al. | 604/8 |
| 7,867,186 B2 * | 1/2011 | Haffner et al. | 604/8 |
| 8,070,708 B2 * | 12/2011 | Rottenberg et al. | 604/9 |
| 8,419,673 B2 * | 4/2013 | Rickard | 604/9 |
| 2003/0139729 A1 * | 7/2003 | Stegmann et al. | 604/540 |
| 2004/0162545 A1 | 8/2004 | Brown et al. | |
| 2004/0193095 A1 * | 9/2004 | Shadduck | 604/8 |
| 2005/0184003 A1 * | 8/2005 | Rodgers et al. | 210/321.75 |
| 2011/0071458 A1 * | 3/2011 | Rickard | 604/9 |
| 2013/0150779 A1 * | 6/2013 | Field | 604/9 |
| 2013/0204177 A1 * | 8/2013 | Field et al. | 604/9 |
| 2013/0211311 A1 * | 8/2013 | Field | 604/9 |

\* cited by examiner

PRE-BIASED MEMBRANE VALVE

BACKGROUND

The present disclosure relates generally to membrane valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development and over-pressurization of the bleb typically induces fibrosis, which leads to increased flow resistance and it is generally the case that this resistance increases overtime. This development and progression of fibrosis reduces or eliminates flow from the anterior chamber, eliminating the capacity of the drainage device to affect IOP. Current drainage devices often employ passive check valves that operate by comparing the IOP and the pressure at the drainage site. Such valves have no mechanism for controlling over-pressurization within the bleb, which may increase to unacceptable levels with over-drainage of aqueous humor into the bleb.

Accordingly, there exists a need for an IOP control system or implant that protects against under-drainage while simultaneously guarding against over-drainage, and consequently minimizes bleb formation and subsequent fibrotic changes. Providing actively responsive valves in the IOP control system that function even in the absence of an energy supply may reduce bleb formation and subsequent fibrotic changes, and thus significantly increase the functional life of the IOP control system. The system and methods disclosed herein overcome one or more of the deficiencies of the prior art.

SUMMARY

In one exemplary aspect, the present disclosure is directed to a method of manufacturing an implantable valve for a fluid system. The method comprises determining a target cracking pressure for the valve of the fluid system, providing an inner wall having a first height and an outer wall having a second height, the first height varying from the second height by a height differential, and attaching a flexible membrane to the outer wall at the second height so that a central zone of the flexible membrane contacts the inner wall at the first height. The inner wall biases the flexible membrane from a neutral condition, and the height differential is selected to provide resistance to displacement from the inner wall until pressure acting on the membrane exceeds the target cracking pressure.

In another exemplary aspect, the present disclosure is directed to a method of manufacturing a plurality of implantable valves having different predetermined target cracking pressures. The method comprises manufacturing a first valve of the plurality of implantable valves and manufacturing a second valve of the plurality of implantable valves. Manufacturing the first valve comprises attaching a first flexible membrane to a first anchoring location at a first height on a first outer wall so that a central zone of the first flexible membrane contacts a first inner wall at a first inner wall height, in a manner that the first inner wall biases the first flexible membrane from a neutral condition. The first height varies from the first inner wall height by a first height differential selected so that the first membrane resists displacement from the first inner wall until pressure acting on the first membrane exceeds a first cracking pressure. Manufacturing the second valve comprises attaching a second flexible membrane to a second anchoring location at a second height on a second outer wall so that a central zone of the second flexible membrane contacts a second inner wall at a second inner wall height, in a manner that the second inner wall biases the second flexible membrane from a neutral condition. The second height varies from the second inner wall height by a second height differential selected so that the second membrane resists displacement from the second inner wall until pressure acting on the second membrane exceeds a second cracking pressure. The first and second flexible membranes have substantially the same structural configuration and elastic properties, and the first height differential differs from the second height differential such that the cracking pressure of the first valve is different than the cracking pressure of the second valve.

In another exemplary aspect, the present disclosure is directed to a valve for a fluidic system having a predetermined target cracking pressure. The fluidic system comprises a housing and a flexible membrane. The housing includes a fluid inlet, a fluid outlet, and a one-piece orifice portion including an inner wall having a first height and an outer wall having a second height. The first height is different than the second height by a height differential, and the outer wall is disposed about the inner wall. The flexible membrane is anchored within the housing to form a reference chamber on a first side of the flexible membrane and a fluid flow channel on a second opposing side of the membrane. The reference chamber has a reference chamber pressure. The flexible membrane is configured to flex and selectively open and close the fluid flow channel to permit fluid to flow from the fluid inlet to the fluid outlet, and the flexible membrane is configured to control flow through the fluid flow channel from the fluid inlet to the fluid outlet by deflecting in response to pressure differentials of the reference chamber pressure and the fluid flow channel pressure acting on the first and second opposing sides of the flexible membrane. The inner wall includes a valve seat disposed in a manner that selectively contacts a central zone of the flexible membrane and seals the fluid inlet with a central zone of the flexible membrane, wherein the height differential displaces the membrane from a neutral condition to a biased condition, resulting in the valve having the predetermined target cracking pressure.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
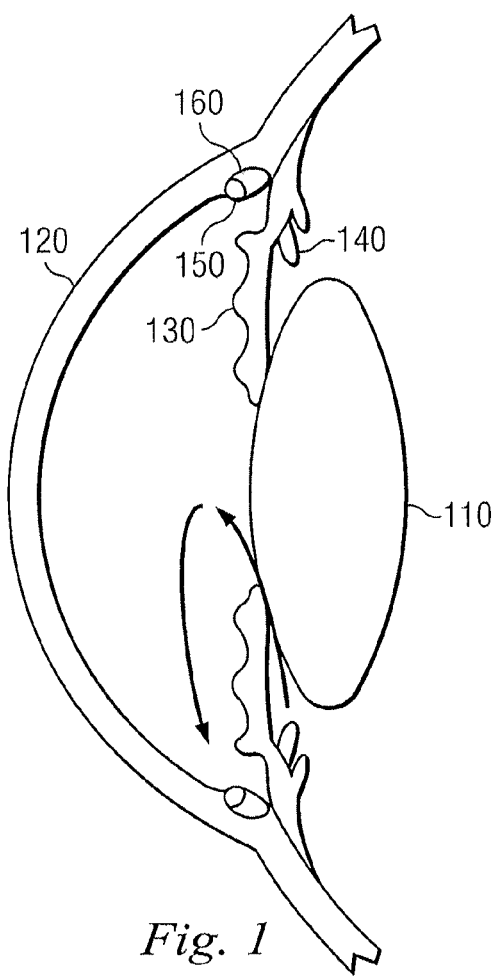
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to membrane valves. In some instances, embodiments of the present disclosure are configured to be part of an IOP control system. The membrane valves disclosed herein include pre-biased membrane valves designed to have a higher or lower cracking pressure in response to pressure differentials acting on the membrane. The membrane valves allow modification of the cracking pressure of the valve without altering the design or production methods of the membrane. In particular, the membrane valves include unequal inner and outer wall heights within the valve housing, which cause the membrane to assume a pre-biased state when the valve is at a neutral state. Thus, valves having different orifice height ratios also have different valve cracking pressures dependant on the pre-biased state of the membrane. As a result, the pre-biased membrane valves disclosed herein may provide a greater degree of control over the membrane deflection profile than that provided by an un-biased membrane valve. Moreover, the height ratio between the inner and outer orifice wall heights may be optimized to provide a particular physical deflection profile as a function of the pressure differentials across the membrane.

Figure 2:
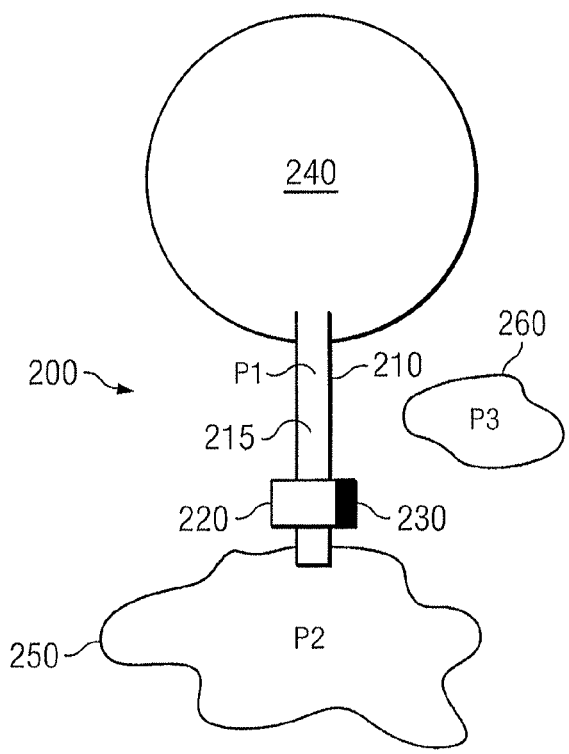
FIG. 2 is a schematic diagram of an exemplary IOP control system according to one embodiment of the present disclosure.

FIG. 2 is a diagram of an exemplary IOP control system 200, including a drainage tube 210, a valve system 220, and a divider 230. In some embodiments, the IOP control system 200 may be positioned within the eye in the subconjunctival pocket between the conjunctiva and the sclera with the anterior border of the valve system 220 positioned approximately 8 to 10 mm posterior to the limbus (the border between the cornea and the sclera). The IOP control system 200 may be held in place within the eye via anchoring structures, the angle of implantation and surrounding anatomy, or by a spring force or other mechanisms that stabilize the IOP control system 200.

In the embodiment pictured in FIG. 2, three areas of pressure interact with the IOP sensor system 200: P1, P2, and P3. Pressure area P1 reflects the pressure of the anterior chamber 240, pressure area P2 reflects the pressure of the drainage site 250 in the subconjunctival space or at least partially in the socket of the eye (and may reflect bleb pressure), and pressure area P3 reflects a reference pressure located remotely from P1 and P2 in a (relatively) dry location 260 (effectively reflecting atmospheric pressure). In some embodiments, pressure area P1 reflects the pressure located in a lumen or tube that is in fluidic communication with the anterior chamber 240.

The IOP control system 200 responds to the pressure differentials between P1, P2, and P3 to control the valve system 220 and thereby throttles the flow rate of aqueous humor through drainage tube 210 to control IOP. More specifically, the various pressure differentials across pressure areas P1, P2, and P3 (P1-P2, P1-P3, P2-P3) drive the valve system 220 and dictate the valve position to throttle the flow rate of aqueous humor through the drainage tube 210 without requiring external power at the valve system 220 to control IOP.

The drainage tube 210 drains aqueous humor from the anterior chamber 240 of the eye. The valve system 220 throttles the flow of aqueous humor through a lumen 215 of the tube 210 as a function of a pressure differential. In the embodiment shown, the pressure area P1 reflects the pressure in the lumen 215 upstream from the valve system 220 and downstream from the anterior chamber 240. The expected discrepancy between the true anterior chamber pressure and that reflected by area P1 when located in a tube downstream of the anterior chamber 240 (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water. Therefore, because there is almost no pressure difference between the anterior chamber 240 and the interior of the tube 210 that is in fluid contact with the anterior chamber 240, pressure area P1 effectively reflects the pressure of the anterior chamber 240.

In some embodiments, a divider 230 separates pressure areas P1 and P2 from pressure area P3. Pressure area P2 reflects the pressure at a drainage site 250. As such, pressure area P2 may be located in a pocket, such as a bleb, that generally contains aqueous humor or in communication with such a pocket, via a tube, for example, and is in a wet location. Pressure area P3 is physically separated from both pressure area P1 and pressure area P2 by divider 230. Divider 230 is a physical structure that separates and isolates the pressure area P1 and the wet drainage site 250 of pressure area P2 from the dry location 260 of pressure area P3. In some embodiments, the divider 230 includes the physical components of the valve system 220, such as parts of a housing. Note that the divider 230 may take many forms, such as, but not limited to, a tube extending pressure area P3 to a remote site or a pocket away from and fluidly independent of the drainage site.

In some embodiments of the present disclosure, the atmospheric pressure area P3 reflects the pressure in an area in close proximity to the eye, and in one embodiment, the pressure area P3 may reflect the pressure in the eye under the conjunctiva. In such cases, pressure area P3 reflects a pressure that can be correlated with atmospheric pressure. Pressure area P3 may also reflect the pressure of a dry portion 260 of the subconjunctival space, separate and apart from the drainage site 250. Regardless of location, pressure area P3 is intended to reflect the reference atmospheric pressure in the vicinity of the eye or at the eye's surface, and when P3 or atmospheric pressure is used herein, it is intended to refer to atmospheric pressure as well as pressure that can be correlated with atmospheric pressure.

Generally, IOP is a gauge pressure reading—the difference between the absolute pressure in the eye (as reflected by P1) and atmospheric pressure (as reflected by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Because the pressure area P3 reflects atmospheric pressure, the difference in pressure between the pressure areas P1 and P3 provides an indication of IOP (the pressure differential between the anterior chamber 240 and the atmospheric pressure). Thus, for accurate control of IOP, it is desirable to have an IOP control system reactive to the pressure differential across the pressure of the anterior chamber (as reflected by P1) and atmospheric pressure in the vicinity of the eye (as reflected by P3). Therefore, in one embodiment of the present disclosure, the IOP control system 200 reacts to the pressure differential across P1 and P3 continuously or nearly continuously so that the actual IOP (as P1-P3 or P1-f(P3)) can be responded to accordingly, where f(P3) indicates some function of P3.

The valve system 220 is connected to the drainage tube 210 and controls the flow of aqueous humor through the lumen 215 of the tube 210 from the anterior chamber 240 to the drainage site 250. The valve system 220 is disposed along, and may form a part of, the drainage tube 210 between the end 270 in the anterior chamber 240 and end 280 at the drainage site 250. In some embodiments, the valve system 220 is disposed within the lumen 215 of the drainage tube 210 between the end 270 and the end 280. The valve system 220 is configured to control the flow of fluid through the drainage tube 210, and thereby control pressure in the eye, including the IOP. For example, when the IOP is high, the valve system 220 may operate to permit increased flow through the drainage tube 210, and when IOP is low, the valve system 220 may operate to decrease the flow through the drainage tube 210. In the embodiment pictured in FIG. 2, the valve system 220 is configured to be continuously responsive to various pressure differentials (P1-P3 or P2-P3) and throttle fluid flow to the drainage site 250 to control IOP as a function of pressure differentials.

In some examples, the valve system 220 may be formed as a part of or utilized in a valve system such as those disclosed in related application Ser. No. 13/315,329, titled "Active Drainage Systems with Pressure-Driven Valves and Electronically-Driven Pump," incorporated herein by reference. The pressure-driven membrane valves disclosed herein may form the downstream valves of the valve system in the incorporated application, titled "Active Drainage Systems with Pressure-Driven Valves and Electronically-Driven Pump."

Figure 3:
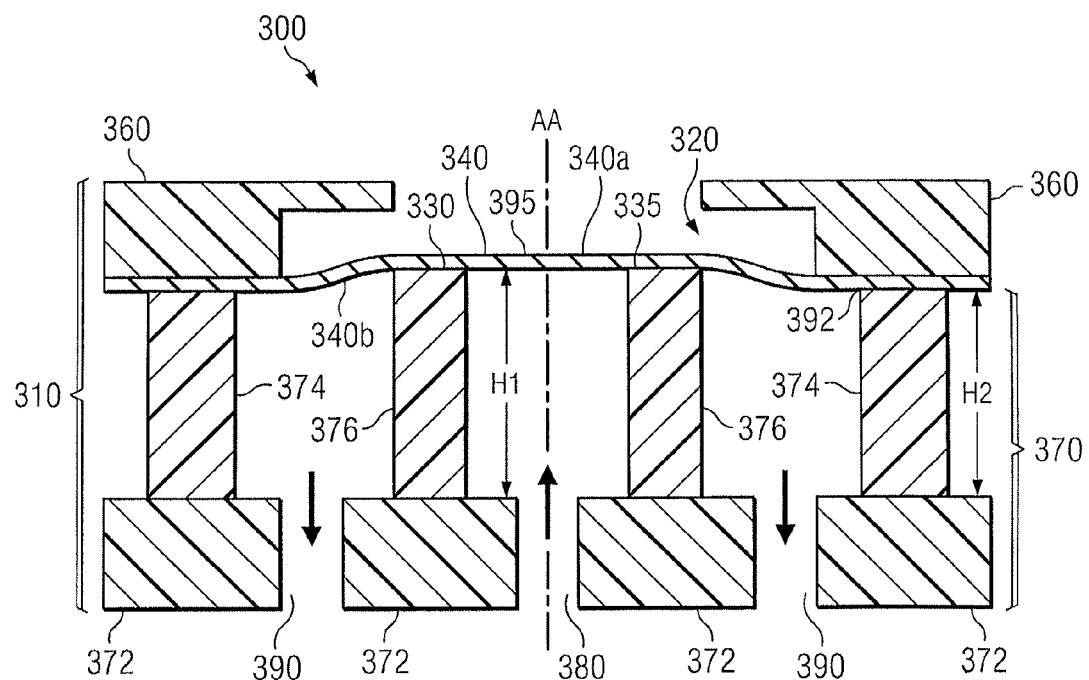
FIG. 3 is a schematic cross-sectional diagram of an exemplary pressure-driven valve in a closed condition according to one embodiment of the present disclosure.

FIG. 3 shows a stylized schematic view of a pressure-driven valve 300 that may form at least a portion of the valve system 220. The pressure-driven membrane valve 300 does not require external power or feedback from electronic pressure sensors to operate. The valve 300 is configured to allow or block aqueous humor flowing from the anterior chamber 240 through the drainage tube 210 to any subsequent valves within the valve system 220 or to the drainage site 250. In the embodiment shown in FIG. 3, the pressure-driven membrane valve 300 includes a housing 310, a reference chamber 320, a valve seat 330, a fluid flow channel 335, and a flow control membrane 340. The fluid flow channel 335 is disposed between the valve seat 330 and the membrane 340, and its size varies depending on the relative position of the membrane 340. In the pictured embodiment, the components of the valve 300 are generally circular in geometry and are symmetric about a center line AA. In alternative embodiments, different geometries for the valve are contemplated, including ovoid and rectangular geometries, for example.

The housing 310 is defined by a membrane housing portion or membrane portion 360 and an orifice portion 370, which mate with one another to form an enclosure within which various other components of the valve 300, such as the flow control membrane 340 and the valve seat 330, are positioned. The orifice portion 370 includes a base 372, an outer wall 374, and an inner wall 376. In the pictured embodiment, the inner and outer walls form concentric, generally annular structures wherein the outer wall 374 concentrically surrounds the inner wall 376. The base 372 includes a fluid inlet 380 and a fluid outlet 390. The fluid inlet 380 is separated from the fluid outlet 390 by the inner wall 376 and the base 372. The valve seat 330 is positioned atop the inner wall 376 between the fluid inlet 380 and the fluid outlet 390 such that fluid flows from the fluid inlet 380, through the fluid flow channel 335, and to the fluid outlet 390.

In alternative embodiments, the housing 310 may be integrally formed of the membrane portion 360 and the orifice portion 370. In alternative embodiments, the portions 360, 370 may cooperate to form the fluid inlet 380 and the fluid outlet 390. The housing 310 may be constructed of any suitable biocompatible material, provided the material is able to maintain constructional integrity at high internal pressures and withstand pressure changes. By way of non-limiting example, in some embodiments, the housing 310 is constructed of silicon and/or silicon dioxide.

The reference chamber 320 is bounded and defined by at least the membrane portion 360 and the flow control membrane 340. The reference chamber 320 is in communication with pressure area P3, which is expected to reflect the atmospheric pressure. In some embodiments, the reference chamber 320 is in communication with the dry subconjunctiva. In alternative embodiments, the reference chamber 320 interfaces with another portion of the eye or to atmospheric pressure directly. Moreover, in alternative embodiments, a plurality of membranes using separate reference chambers (and reference chamber pressures) is contemplated for use in the valve 300.

In the pictured embodiment in FIG. 3, the inner wall 376 and the outer wall 370 are shaped as generally annular or toroid, concentric components. The inner wall 376 is positioned such that the central aperture of the inner wall 376 and the fluid inlet 380 are co-aligned about the central axis AA. The valve seat 330 is formed by the top of the inner wall 376 and is positioned to concentrically overlie the fluid inlet 380. The central aperture of the valve seat 330 serves as the entrance to the fluid flow channel 335. The valve seat 330 and the inner wall 376 are shaped and configured such that when the flow control membrane 340 rests on the valve seat 330, the valve 300 is in a closed condition. Thus, the central aperture of the inner wall 376 serves as both the exit of the fluid inlet 380 and the entrance to the fluid flow channel 335, and when the flow control member 340 rests on the inner orifice wall 376, the valve 300 is in a closed position.

In various embodiments, the inner wall 376 may be configured as an integral extension of the base 372, or may be a separate component of the orifice portion 370, and may be constructed (e.g., molded, machined, or built using Micro-Electro-Mechanical Systems (MEMS) microfabrication techniques) at the same time as the orifice portion 370. For example, the inner wall 376 may be fabricated by micromachining or MEMS techniques at the same time, or in processing steps before or after the fabrication of the orifice portion 370, depending on the exact nature of the fabrication process used (such as whether the process steps used for these features are primarily additive or subtractive in nature).

As indicated above, the fluid flow channel 335 comprises the circumferential gap that arises between the valve seat 330 and the flow control membrane 340 when the flow control member 340 deflects away from the valve seat 330 toward the reference chamber 320. As shown in FIG. 3, the fluid flow channel 335 can in some areas be restricted to zero or near-zero size in some dimension (e.g., in height, as drawn in FIG. 3) when the flow control membrane 340 rests on the valve seat 330 and the valve 300 is in a closed condition.

Figure 4:
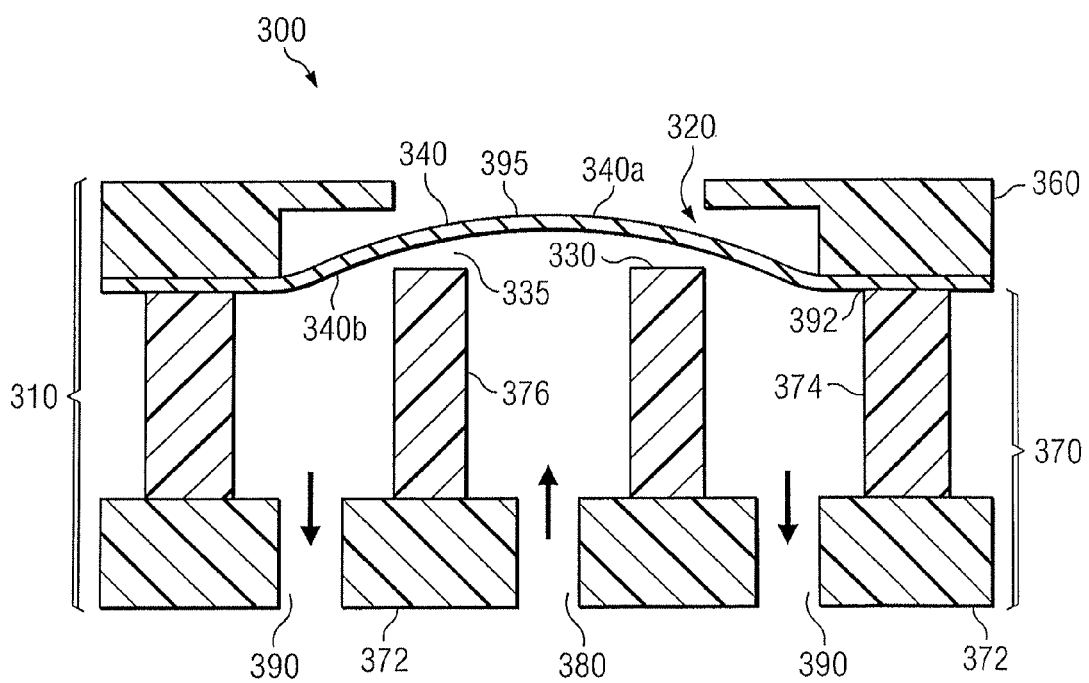
FIG. 4 is a schematic cross-sectional diagram of the pressure-driven valve shown in FIG. 3 in an open condition according to one embodiment of the present disclosure.

As shown in FIG. 4, however, the fluid flow channel 335 is not restricted or is less restricted when the flow control membrane 340 deflects off the valve seat 330 on the inner wall 376 into the reference chamber 320 and the valve 300 is in an open condition. When the valve 300 is in an open condition, the fluid flow channel 335 is generally a constant height around the annular sealing surface of valve seat 330 (i.e., the gap between the inner wall 376 and the membrane 340 is generally uniform) at any given time.

The flow control membrane 340 comprises a flexible, deformable, fluid-tight membrane or diaphragm that provides valve functionality by deflecting in response to pressure differentials across its two opposing sides. The flow control membrane 340 includes two sides, a side 340a and an opposite side 340b. In one embodiment, the sides 340a and 340b are substantially parallel. The side 340a faces the reference chamber 320, and consequently conveys the pressure of pressure area P3. The side 340b is in fluidic communication with the lumen 215 of the drainage tube 210 (shown in FIG. 2), and in particular the fluid inlet 380, and consequently conveys the pressure of pressure area P1. The side 340b of the flow control membrane 340 is configured to selectively seal against the valve seat 330 atop the inner wall 376 and thereby close the valve 300 when the pressure against the side 340a sufficiently outweighs the pressure against the side 340b. As will be explained in further detail below, the flow control membrane 340 deflects in response to pressure differences between the fluid inlet 380 and the reference chamber 320 to at least partially open and close the valve 300 by changing the dimensions of the fluid flow channel 335.

The flow control membrane 340 may be unitarily made or formed by stamping, molding, vapor deposition, or any other suitable means known in the art from any suitable biocompatible, flexible material. The membrane 340 can be constructed of any suitable biocompatible material that can move, flex, deform, or deflect in response to differential pressures. The material may comprise a thermoplastic material, an elastomeric material, a thermoplastic elastomer, materials such as those used in semiconductor and MEMS processing such as Silicon or Silicon Nitride, or any biocompatible metals such as gold, or any combinations of the foregoing. In some embodiments, the flow control membrane 340 is constructed using the techniques common to fabricate a MEMS membrane, such as, but not by way of limitation, a Parylene membrane. In addition to being actuatable by pressure differentials across the membrane, MEMS membranes may also be actuated by several other means, including, but not by way of limitation, electrostatically, magnetically, and thermally.

For purposes of practicality, the flow control membrane 340 should be thick enough to be durable and resistant to corrosion and leakage. However, the membrane 340 should also be thin enough to provide the necessary flexibility and deflection capabilities which are required in a substantially planar membrane designed for use in a pressure-responsive IOP control system 200. Membrane thickness, material, and diameter, residual stress, and the number, placement, and depth of possible corrugations, all affect the cracking pressure of the flow control membrane 340.

As shown in FIG. 3, the flow control membrane 340 is securely held in place within the housing 310 so that it will not be displaced by the force of the fluid flowing through the valve 300. The valve 300 may be in the closed configuration, as shown in FIG. 3, in a scenario where the pressure difference between the pressures in the fluid in the drainage tube 210 (P1) and the reference chamber 320 (P3) is generally lower than a target value—for example, 6 mm Hg (corresponding the lowest safest IOP level). Conversely, the valve 300 may be in the open configuration, as shown in FIG. 4, in a scenario where the pressure difference between the pressure in the fluid in the drainage tube 210 (P1) and the reference chamber 320 (P3) is generally higher than a target value—for example, 12 mm Hg+/−1 mm Hg (corresponding to the highest possible IOP acceptable for a given patient prior to allowing drainage). Note that the desired target value will be different from patient to patient, thus necessitating multiple permutations of the membrane valve design to support the needs of the glaucoma patient population (i.e., target values ranging from 7-18 mm Hg).

The valve 300 is configured as a flow control valve that can completely or partially block the flow of aqueous humor by deflecting the flow control membrane 340 completely or partially across the fluid flow channel 335. The housing 310 is configured to connect with drainage tube 210 such that deflection of the flow control membrane 340 at least partially opens and closes the lumen 215 to the outflow of aqueous humor. As described above, the position of the flow control membrane 340 determines whether the valve 300 is in an open, partially open, or closed condition. When the membrane 340 seals against the valve seat 330, the valve 300 is in a closed condition. When the membrane 340 deflects away from the valve seat 330, the valve 300 is in an open or partially open condition.

As part of the valve system 220, the valve 300 is in fluidic communication with the drainage tube 210 (shown in FIG. 2) and in communication with the dry subconjunctiva. In particular, the fluid inlet 380 fluidically interfaces with the drainage tube 210 (reflecting pressure area P1). The reference chamber 320 interfaces with the subconjunctiva isolated from the drainage location (reflecting pressure area P3). The flow control membrane 340 extends across the housing 310 to form a sealed separation between the reference chamber 320 and the fluid inlet 380, thereby creating an effective separation between pressure areas P3 and P1, respectively. Accordingly, as the pressure increases against one side of the flow control membrane 340, the pressure increase acts to displace the flow control membrane 340 in the direction away from the higher pressure. The fluid inlet 380 conveys the pressure of pressure area P1 on one side 340b of the flow control membrane 340. The reference chamber 320 conveys the pressure of pressure area P3 on the opposite side 340a of the flow control membrane 340.

In the embodiment pictured in FIG. 3, the flow control membrane 340 is anchored between the membrane portion 360 and the orifice portion 370. More specifically, a peripheral zone 392 of the flow control membrane 340 is sandwiched between the membrane portion 360 and the outer wall 374 of the orifice portion 370. In other embodiments, the flow control membrane 340 is anchored within either the membrane portion 360 or the orifice portion 370. The membrane portion 360, the membrane 340, and the orifice portion 370 are secured into this arrangement by any of a variety of known methods, including by way of non-limiting example, adhesive, welding, mechanical fasteners, or adhesion techniques associated with MEMS microfabrication. Regardless of how the membrane 340 is secured within the housing 300, at least a portion of the housing 300 applies a compressive force to a periphery of the membrane 340 to maintain it in a desired position relative to the valve seat 330 or inner wall 376.

As mentioned above, the flow control membrane 340 directs flow by deflecting within the housing 310 of the valve 300 in response to the pressure differential between the fluid chamber pressure (as reflected by pressure area P1) against one side 340b of the flow control membrane 340 and the subconjunctival pressure isolated from the drainage location (as reflected by pressure area P3, which is expected to correspond to atmospheric pressure) against the opposite side 340a of the flow control membrane 340. The cracking pressure of the valve 300 is the pressure threshold above the pressure of the reference chamber 320 (P3) at which the membrane 340 deflects off the valve seat 330 atop the inner wall 376. In particular, if the IOP exceeds the cracking pressure of the flow control membrane 340, then the valve 300 will assume an open condition and allow free flow to regulate the IOP down to the desirable range. Otherwise, the valve 300 remains in a closed condition because the IOP (P1-P3) or pressure difference across the membrane 340 is below the cracking pressure.

The cracking pressure is dependent on the type, size, and stiffness of the flow control membrane 340 and the structure of the valve housing 310. Accordingly, the cracking pressure may be preselected by controlling these parameters during manufacturing or assembly processes.

In one example, these dimensions are selected so that the valve 300 remains closed when the IOP (P1-P3) is below the desired cracking pressure. After implantation of the valve 300, the patient's IOP will begin to approximate the cracking pressure of the valve 300. Therefore, the surgeon may select a valve 300 having a particular cracking pressure based on the most appropriate or desired IOP range for the treatment of a particular condition.

As illustrated in the embodiment shown in FIG. 3, the membrane 340 and the other features of the valve are designed with a pre-biased condition such that the valve 300 is normally closed (for instance when P1-P3 is at or near zero or some other desired value) and its biased condition is such that the above mentioned open and closed pressure requirements are met. Such biasing can be achieved by any of a variety of techniques. In some embodiments, biasing is achieved by varying the heights of the inner wall 376 and the outer wall 374 to displace the vertical position of a central zone 395 the flow control membrane 340 relative to the peripheral zone of the membrane 340, thereby affecting the cracking pressure of the valve.

Varying the height and other dimensions of the inner wall 376 relative to the height and other dimensions of the outer orifice wall 374 affects the amount and rate of fluid flow through the valve 300. For example, in the pictured embodiment, the valve 300 is pre-biased to have a higher cracking pressure by increasing the ratio between the inner orifice wall height and the outer orifice wall height. In the pictured embodiment, the inner wall 376 is shaped to have a height H1 that is greater than a height H2 of the outer orifice wall 374. Accordingly, the inner wall 376 forms the valve seat 330 at a raised position within the housing 310. A valve having this configuration has a higher cracking pressure than a valve utilizing the same pressure driven valve membrane within a housing where the difference between H1 and H2 is zero.

Increasing the ratio between the height H1 of the inner wall 376 and the height H2 of the outer wall 374 forces the membrane 340 into a deflected state at rest and yields a higher valve cracking pressure. In the pictured embodiment, the increased height H1 of the inner wall 376 relative to the height H2 of the outer wall pre-biases the membrane 340 and thereby raises higher cracking pressure of the valve 300. Thus, varying the heights of the inner wall 376 and the outer wall 374 permits increased design flexibility and flow control for the valve 300. In other words, the cracking pressure of the valve may be preselected or predetermined during the manufacturing process by adjusting the structural relationship of membrane, the inner wall height, and outer wall height, without altering the physical properties of the membrane itself. The surgeon would be able to select a valve having an optimal cracking pressure to treat a particular patient having a particular ophthalmic condition and target IOP.

FIG. 3 illustrates the valve 300 in a closed, flow-blocking position, wherein the flow control membrane 340 is deflected towards the valve seat 330 to seal the fluid outlet 390, thereby preventing the flow of fluid from the fluid inlet 380 into the fluid outlet 390. The valve 300 is in a closed position because the IOP (P1-P3) is not in excess of the cracking pressure of the valve 300, and the pressure of the reference chamber 320 forces the membrane 340 against the valve seat 330. The flow control membrane 340 is resting on the sealing surface of the valve seat 330, thereby blocking the flow of aqueous humor from the fluid inlet 380 to the fluid outlet 390 and through the drainage tube 210. It is desirable not to allow the IOP to drop below a certain threshold, for example, 6 mmHg. Any intraocular pressure below such a threshold is considered hypotonous pressure and is dangerous to the eye. The valve system 220 is self-limiting because the pressure-driven valve 300 will not open unless the pressure differential across the valve 300 overcomes the cracking pressure of the valve. Accordingly, if the IOP (P1-P3) is lower than the cracking pressure of the flow control membrane 340, then the valve 300 will not open and aqueous humor will not leave the anterior chamber 240 through the IOP control system 200.

FIG. 4 illustrates the valve 300 in an open, flow-permitting condition. When the IOP (P1-P3) is in excess of the cracking pressure of the valve 300 (equivalent to the target IOP), the membrane 340 rises off the valve seat 330 and the valve 300 opens, thereby allowing aqueous humor to flow through the drainage tube 210 from the fluid inlet 380 to the fluid outlet 390 in the direction of possible additional flow regulating valves and the drainage site 250 (shown in FIG. 2). Accordingly, the valve 300 is in an open condition because the IOP (P1-P3) is in excess of the cracking pressure of the flow control membrane 340 (equivalent to the target IOP), for example 8 mm Hg+/−2 mm Hg. The flow control membrane 340 allows flow through the tube 210 by deflecting off the valve seat 330 and into the reference chamber 320 in response to the pressure differential between the anterior chamber pressure (as reflected by pressure area P1 in the fluid inlet 380) against one side 340b of the flow control membrane 340 and the dry subconjunctival pressure (as reflected by pressure area P3 in the reference chamber 320) against the opposite side 340a of the flow control membrane 340. Because the valve 300 is in an open condition, the aqueous humor can flow through the drainage tube 210 from the fluid inlet 380 to the fluid outlet 390 in the direction of any remaining flow control devices (including, without limitation, valves, pumps, and/or other flow-regulating devices) and the drainage site 250. This ensures that drainage of the aqueous humor can occur through the drainage tube 210 if the IOP is elevated. In alternate embodiments, the valve 300 may have any number of fluid inlets 380 and fluid outlets 390.

The resistance to flow of the flow control member 340 decreases with greater displacement. Accordingly, in higher pressure situations, the valve 300 will assume a more open condition than in lower pressure situations. The higher the pressure of the fluid within the fluid inlet 380 (P1) in comparison with the pressure of the reference chamber 320 (P3), the more the flow control member 340 deforms, thereby enlarging the entrance to and the dimensions of the fluid flow channel 335 and allowing greater amounts of aqueous humor to flow from the fluid inlet 380, across the valve seat 330, and through the fluid outlet 390. Conversely, the lower the pressure of the fluid within the fluid inlet 380 (P1) in comparison with the pressure of the reference chamber 320 (P3), the more the flow control membrane 340 deforms to block the entrance to the fluid flow channel 335 and thus reduce the dimensions available for flow within the fluid flow channel 335, thereby in one or both ways restricting aqueous humor from entering the fluid flow channel 335. That is, the flow resistance can be realized by two possible mechanisms: reducing the size of the fluid inlet 380 and reducing the dimensions of the flow channel 335. Decreasing size of the fluid inlet 380 allows a pressure drop because of a nozzling effect (a portion of pressure drop occurs even within inviscid flow theory). Reducing the channel height of flow channel 335 can provide significant resistance for the length of flow channel 335 because of viscous losses.

Figure 5:
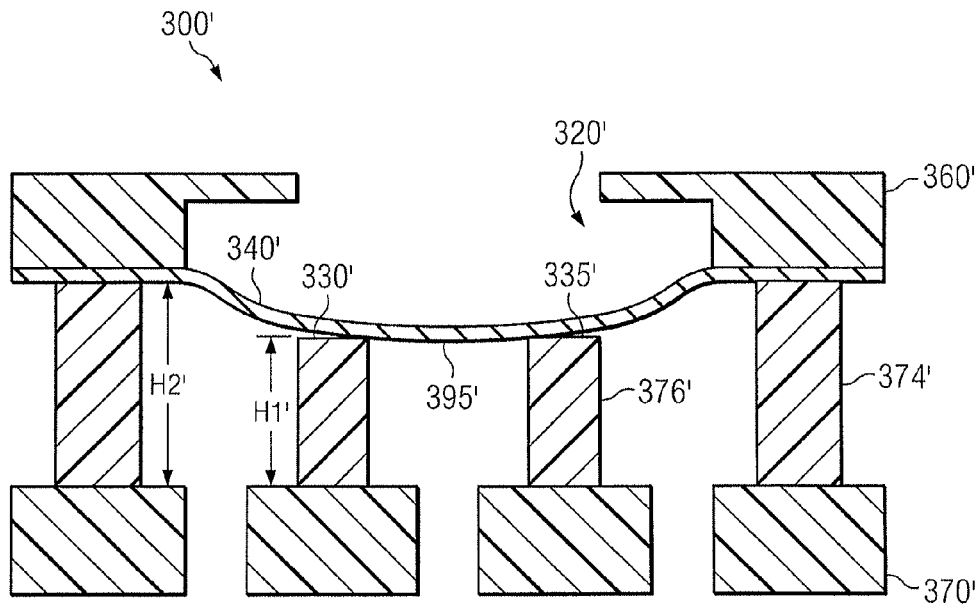
FIG. 5 is a schematic cross-sectional diagram of another exemplary pressure-driven valve in a closed condition according to one embodiment of the present disclosure.

FIG. 5 shows a valve 300', which is similar to the valve 300 except for the differences noted herein. The individual components of the valve 300', including a valve seat 330', a flow channel 335', a flow control membrane 340', a membrane portion 360', an orifice portion 370', an outer wall 374', and an inner wall 376', are similar to the corresponding components of the valve 300. The flow control membrane 340' is anchored between the membrane portion 360' and the orifice portion 370'.

The inner wall 376' is shaped to have a height H1' that is less than a height H2' of the outer wall 374'. In such instances, as shown in FIG. 5, the inner wall 376' forms the valve seat 330' at a lowered position within the housing 310 (as compared to, for example, the valve 300 pictured in FIGS. 3 and 4). The inner wall 376' is shaped and configured such that a central zone 395' of the flow control membrane 340' is generally relaxed onto the valve seat 330' atop the inner wall 376' when the valve 300' is at rest or at a neutral condition. That is, the vertical position of the central zone 395' of the membrane 340' is positioned below the anchored vertical position of a peripheral zone 392' of the membrane 340' when the valve 300' is at rest or at a neutral condition.

Lowering the ratio between the height H1' of the inner wall 376' and the height H2' of the outer wall 374' yields a lower cracking pressure. In the pictured embodiment, the decreased height HP of the inner wall 376' relative to the height H2' of the outer wall pre-biases the membrane 340' and thereby lowers cracking pressure of the valve 300'. Thus, the cracking pressure of the valve 300' is lower than the cracking pressure of the valve 300 because of different pre-biasing effects achieved by varying the ratios of inner wall heights to outer wall heights in the valves 300, 300'. It should also be noted that a neutral membrane position at and between that depicted in FIG. 5 and at a height difference of zero (H1−H2=0) may be utilized to achieve a desired cracking pressure.

Figure 6:
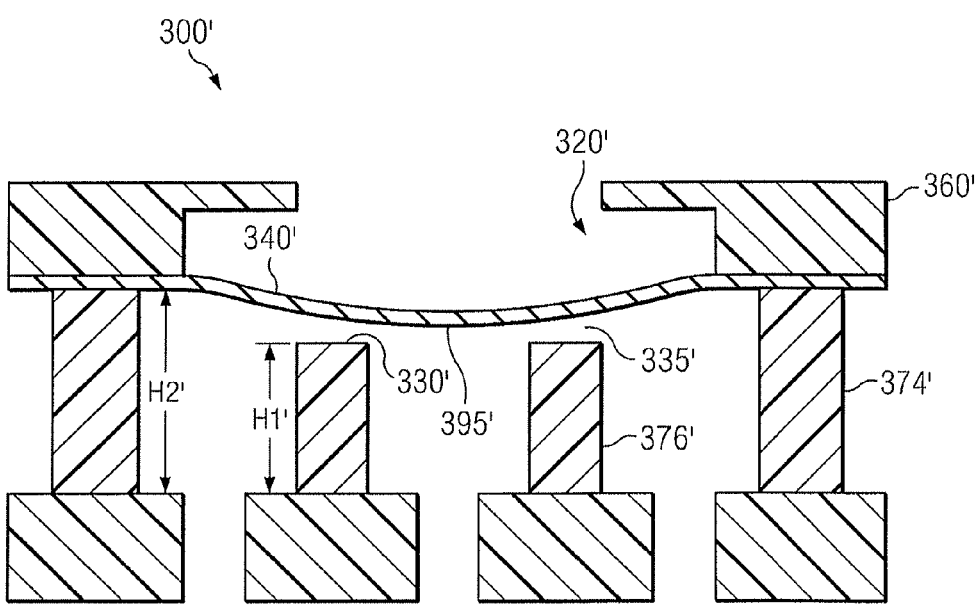
FIG. 6 is a schematic cross-sectional diagram of the pressure-driven valve shown in FIG. 5 in an open condition according to one embodiment of the present disclosure.

FIG. 6 illustrates the valve 300' in an open condition, wherein the flow control membrane 340' is deflected away from the valve seat 330' toward the reference chamber 320', thereby allowing the flow of fluid from the fluid inlet 380' into the fluid outlet 390'. The valve 300' is in an open condition because the IOP (P1-P3) is in excess of the cracking pressure of the flow control membrane 340' (equivalent to the target IOP), for example 10 mm Hg+/−2 mm Hg.

Though the pressure-driven valves 300, 300' are depicted as comprising a disk-like flow control membrane, the valves 300, 300' may be comprised of any of a number of different flow control elements that meter, restrict, or permit the flow of aqueous humor from the anterior chamber 240 to the drainage site 250. For example, trapped gaseous medium can be used in conjunction with a compliant membrane to enable the pressure-driven valves. In some embodiments, the flow control membrane 340 may be used in conjunction with and/or actuate a pump. In addition, the valve 300 may be positioned anywhere in fluid communication with the drainage tube 210, whether within or along the drainage tube 210. To ensure biocompatibility, the valves 300, 300' can be coated or encapsulated in a biocompatible material including, but not by way of limitation, polypropylene, silicone, parylene, or other known biocompatible materials. In some embodiments, the valves 300, 300' can be coated with a biologically active compound or drug.

Manufacture of a plurality of implantable valves having different predetermined target cracking pressures in accordance with the present disclosure may be carried out by the following exemplary process. First, a flexible membrane is selected for use within the plurality of valves. A target cracking pressure is identified for the first valve of the plurality of valves. Next, the appropriate height differential or ratio between the inner wall and the outer wall of the orifice portion of the valve is calculated. The appropriate height differential is one that pre-biases the membrane within the valve housing to create a valve with the pre-selected target cracking pressure. In particular, the height differential is selected to provide resistance to displacement from the inner wall until the pressure acting on the membrane reaches the target cracking pressure. Because the inner wall defines the fluid inlet spanned by the flexible membrane, the height differential takes into account the diameter of the fluid inlet to achieve a balance between fluid inlet diameter and resistance to deflection to achieve the target cracking pressure. Thus, the inlet size (i.e., inlet diameter) as well as various characteristics of the membrane factor into selecting the appropriate height differential to create the desired cracking pressure.

Once the appropriate height differential is calculated, the orifice portion of the first valve is manufactured to include a first inner wall having a first inner wall height and a first outer wall having a first height, wherein the first inner wall height varies from the first height by the calculated height differential. During assembly of the first valve, a first flexible membrane is attached to a first anchoring location at the first height on the first outer wall so that a central zone of the first flexible membrane contacts the first inner wall at the first inner wall height, in a manner that the first inner wall biases the first flexible membrane from a neutral condition. In some instances, the first flexible membrane is anchored between the orifice portion and the membrane portion such that the membrane is pre-biased by the configuration of the orifice portion. In some instances, attaching the first flexible membrane to the first outer wall includes clamping peripheral edges of the flexible membrane to a top portion of the outer wall.

In particular, the first height varies from the first inner wall height by a first height differential selected so that the first flexible membrane resists displacement from the first inner wall until pressure acting on the first membrane exceeds a first cracking pressure. For example, in some embodiments, where the inner wall has a greater height than the outer wall, the central zone of the membrane is forced into a deflected state toward the reference chamber (even in the absence of pressure acting on the valve). As explained above, this configuration creates a valve with a higher cracking pressure than a valve having an unbiased condition.

A second valve may be manufactured to have a different predetermined cracking pressure than the first valve, although the second valve and the first valve both utilize the same type of membrane. For example, in some instances, the first and second flexible membranes have substantially the same structural configuration and elastic properties. First, a second target cracking pressure is identified, wherein the second cracking pressure is different than the first target cracking pressure. Next, the appropriate height differential or ratio between the inner wall and the outer wall of the orifice portion of the second valve is calculated as described above with reference to the first valve. In particular, the appropriate height differential is one that pre-biases the membrane within the valve housing to create a valve with the second pre-selected target cracking pressure.

Once the appropriate height differential for the second valve is calculated, the orifice portion of the second valve is manufactured to include a second inner wall having a second inner wall height and a second outer wall having a second height, wherein the second inner wall height varies from the second height by the calculated height differential. During assembly of the second valve, a second flexible membrane is attached to a second anchoring location at the second height on the second outer wall so that a central zone of the second flexible membrane contacts the second inner wall at the second inner wall height, in a manner that the second inner wall biases the second flexible membrane from a neutral condition. In some instances, the second flexible membrane is anchored between the orifice portion and the membrane portion such that the membrane is pre-biased by the configuration of the orifice portion. In particular, the second height varies from the second inner wall height by a second height differential selected so that the second membrane resists displacement from the second inner wall until pressure acting on the second membrane exceeds a second cracking pressure.

The first height differential differs from the second height differential such that the cracking pressure of the first valve is different than the cracking pressure of the second valve. Thus, a plurality of valves having the same type of membrane and a variety of different cracking pressures may be manufactured by varying the height differential between the inner and outer walls of the orifice portions of each valve housing.

In some instances, the first valve and the second valve are sized for implantation in an eye. In some instances, a drainage tube is attached to a passage through the inner wall of the valve, and the passage is oriented so that the passage is substantially perpendicular to the flexible membrane. In some instances, the inner wall of the valve forms a boss.

In some instances, a third valve (or series of valves) may be manufactured to have a different type of membrane as well as a different target cracking pressure than the first and second valves. To calculate the appropriate height differential or ratio between the inner wall and the outer wall of the orifice portion of the third valve, various characteristics of the membrane and the orifice size are taken into account. In particular, the appropriate height differential is one that pre-biases the membrane within the valve housing to create a valve with the third pre-selected target cracking pressure. The third valve may be manufactured and assembled in the same fashion as described above in relation to the first and second valves.

The devices and systems described herein allows the user to modify the cracking pressure of a pressure-driven membrane valve without modifying the design or production methods of the membrane itself. Instead, the cracking pressure of the valve is affected by the structural relationship between the membrane and the valve housing. Specifically, increasing the ratio between the inner wall height and the outer wall height increases the cracking pressure of the valve, and, conversely, decreasing the ratio between the inner wall height and the outer wall height decreases the cracking pressure of the valve. The embodiments described herein allow for multiple permutations of valve cracking pressures by changing wall height ratios of the housing.

Embodiments in accordance with the present disclosure may be used in a variety of applications to regulate flow and/or pressure. For example, but not by way of limitation, embodiments of the present disclosure may be utilized to regulate flow and/or pressure as part of a microanalytical system, a dialysis system, a process control system, a drug delivery system, a solar thermal system, a cooling system, and/or a heating system. Some embodiments of the present disclosure may be utilized to regulate pressure and/or flow in a variety of fluidic systems such as, but not by way of limitation, the urinary tract, the brain (e.g., to regulate intracranial pressure), and the circulatory/renal system (e.g., as part of a dialysis system). Moreover, some embodiments are shaped and configured for implantation in a patient, while others are not.

In some instances, the valves described herein may be available to the medical professional in a kit containing several valves having different cracking pressures. Thus, a medical professional could implant a valve having a first cracking pressure into a patient, observe the resultant flow control and IOP ranges achieved in the patient, and subsequently decide to maintain or change the valve implant depending upon the results.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A valve for a fluidic system having a predetermined target cracking pressure, comprising:
    a housing including a fluid inlet, a fluid outlet, and a one-piece orifice portion including an inner wall having a first height and an outer wall having a second height, the first height being different than the second height by a height differential, the outer wall being disposed about the inner wall; and
    a flexible membrane anchored within the housing to form a reference chamber on a first side of the flexible membrane and a fluid flow channel on a second opposing side of the membrane, the reference chamber having a reference chamber pressure, the flexible membrane being configured to flex and selectively open and close the fluid flow channel to permit fluid to flow from the fluid inlet to the fluid outlet, the flexible membrane configured to control flow through the fluid flow channel from the fluid inlet to the fluid outlet by deflecting in response to pressure differentials of the reference chamber pressure and the fluid flow channel pressure acting on the first and second opposing sides of the flexible membrane,
    wherein the flexible membrane is anchored to the housing in a valve-closed position when the pressure differential is zero,
    wherein the inner wall includes a valve seat disposed in a manner that selectively contacts a central zone of the flexible membrane and seals the fluid inlet with a central zone of the flexible membrane, wherein the height differential displaces the membrane from a neutral condition to a biased condition, resulting in the valve having the predetermined target cracking pressure.

2. The valve of claim 1, the housing further including a membrane portion, wherein a peripheral zone of the flexible membrane is anchored between the membrane portion and the outer wall.

3. The valve of claim 1, wherein the first height of the inner wall is greater than the second height of the outer wall.

4. The valve of claim 1, wherein the first height of the inner wall is less than the second height of the outer wall.

5. The valve of claim 1, wherein the fluid flow channel comprises a gap between the valve seat and the flexible membrane.

6. The valve of claim 1, wherein the flexible membrane comprises a flexible, fluid-tight membrane configured to deflect away from the valve seat in response to an elevated pressure.

7. The valve of claim 6, wherein the flexible membrane comprises a circular membrane.

8. The valve of claim 1, wherein the flexible membrane is configured to control flow through the fluid flow channel by deflecting in response to pressure differentials between an anterior chamber of the eye and atmospheric pressure acting on the flexible membrane.

9. A valve for a fluidic system having a predetermined target cracking pressure, comprising:
    a housing including an inner wall surrounding a fluid inlet and an outer wall disposed about the inner wall to define a fluid outlet between the inner wall and the outer wall, the inner wall having a first height and the outer wall having a second height, the first height being greater than the second height by a height differential; and
    a flexible membrane anchored within the housing to form a reference chamber on a first side of the flexible membrane and a fluid flow channel on a second opposing side of the membrane, the reference chamber having a reference chamber pressure and the fluid flow channel having a fluid flow channel pressure, the flexible membrane being configured to flex and selectively open and close the fluid flow channel to permit fluid to flow from the fluid inlet to the fluid outlet, the flexible membrane configured to control flow through the orifice portion by deflecting in response to a pressure differential across the flexible membrane of the reference chamber pressure and the fluid flow channel pressure acting on the first and second opposing sides of the flexible membrane,
    wherein the height differential displaces the membrane from a neutral condition to a biased condition, resulting in the valve having the predetermined target cracking pressure.

10. The valve of claim 9, wherein the inner wall includes a valve seat disposed in a manner that selectively contacts a central zone of the flexible membrane and seals the fluid inlet with the central zone of the flexible membrane.

11. The valve of claim 10, wherein a peripheral zone of the flexible membrane is anchored to the outer wall.

12. The valve of claim 9, wherein the flexible membrane is anchored to the housing in a valve-closed position when the pressure differential is zero.

13. The valve of claim 10, the housing further including a central aperture defined by the inner wall, the central aperture being aligned with the fluid inlet about a longitudinal axis extending through the central zone of the flexible membrane at a substantially perpendicular angle.

14. The valve of claim 13, wherein the flexible membrane is configured to selectively open and close the fluid flow channel to permit fluid to flow from the fluid inlet, through the central aperture, through the fluid flow channel, and out the fluid outlet.

15. The valve of claim 10, wherein the fluid flow channel comprises a gap between the valve seat and the flexible membrane when the pressure differential exceeds the target cracking pressure.

16. The valve of claim 10, wherein the flexible membrane comprises a flexible, fluid-tight membrane configured to deflect away from the valve seat in response to an elevated inlet pressure.

17. The valve of claim 16, wherein the flexible membrane comprises a circular membrane.

18. The valve of claim 9, wherein the reference chamber pressure is atmospheric pressure and wherein the fluid flow channel pressure corresponds to pressure in the anterior chamber of an eye.

* * * * *